United States Patent
Biermann et al.

(10) Patent No.: US 11,839,736 B2
(45) Date of Patent: Dec. 12, 2023

(54) CASSETTE FOR A FLOW CONTROL APPARATUS

(71) Applicant: KPR U.S., LLC, Mansfield, MA (US)

(72) Inventors: Wayne Biermann, St. Charles, MO (US); Lester Paul Trelford, St. Louis, MO (US)

(73) Assignee: KPR U.S., LLC, Mansfield, MA (US)

( * ) Notice: Subject to any disclaimer, the term of this patent is extended or adjusted under 35 U.S.C. 154(b) by 769 days.

(21) Appl. No.: 16/696,959

(22) Filed: Nov. 26, 2019

(65) Prior Publication Data

US 2020/0164141 A1 May 28, 2020

Related U.S. Application Data

(60) Provisional application No. 62/771,463, filed on Nov. 26, 2018.

(51) Int. Cl.
*A61M 5/14* (2006.01)
*A61M 5/142* (2006.01)

(52) U.S. Cl.
CPC ...... *A61M 5/1413* (2013.01); *A61M 5/14228* (2013.01); *A61M 2205/121* (2013.01); *A61M 2205/14* (2013.01); *A61M 2205/3334* (2013.01); *A61M 2205/6054* (2013.01); *A61M 2240/00* (2013.01)

(58) Field of Classification Search
CPC ...... A61M 1/15; A61M 1/152; A61M 1/1524; A61M 1/153; A61M 1/154; A61M 1/155; A61M 1/156; A61M 1/159; A61M 1/28; A61M 1/281; A61M 1/282; A61M 1/284; A61M 1/3401; A61M 1/3622; A61M 1/36222; A61M 1/362227; A61M 1/36223; A61M 1/36224; A61M 1/36225; A61M 1/36226; A61M 1/72; A61M 3/0201; A61M 5/1413; A61M 5/14228; A61M 5/14232; A61M 2205/12; A61M 2205/121; A61M 2205/127; A61M 2205/14; A61M 2205/6054
See application file for complete search history.

(56) References Cited

U.S. PATENT DOCUMENTS

| | | | |
|---|---|---|---|
| 5,057,081 A * | 10/1991 | Sunderland | F04B 43/1253 D24/111 |
| 5,540,668 A | 7/1996 | Wilson, Jr. et al. | |
| 2005/0095155 A1* | 5/2005 | Blight | A61M 3/0216 417/477.13 |

(Continued)

FOREIGN PATENT DOCUMENTS

EP 2221084 A1 8/2010

*Primary Examiner* — Kami A Bosworth
(74) *Attorney, Agent, or Firm* — ArentFox Schiff LLP

(57) ABSTRACT

A cassette for use with a pumping apparatus having a pumping system for engaging a pump set includes a cassette body configured for releasable attachment to the pumping apparatus to mount the cassette on the pumping apparatus. The cassette body has at least one mounting formation. At least one identification member is mounted on the cassette body by the mounting formation of the cassette body. The identification member and mounting formation are formed to mount the identification member in any one of a plurality of predetermined orientations. Each predetermined orientation indicates a different functional configuration of the pump set.

20 Claims, 14 Drawing Sheets

(56) References Cited

U.S. PATENT DOCUMENTS

| | | |
|---|---|---|
| 2005/0267418 A1* | 12/2005 | Fournie ............ A61M 5/14232 604/249 |
| 2005/0267439 A1* | 12/2005 | Harr ................ A61M 5/16813 604/131 |
| 2010/0211022 A1 | 8/2010 | Harr et al. |
| 2014/0135731 A1* | 5/2014 | Breitweiser ......... F04B 43/0072 604/151 |
| 2014/0261808 A1 | 9/2014 | Brouwer et al. |
| 2015/0000669 A1* | 1/2015 | Miller .................. F16L 19/005 285/91 |
| 2015/0018780 A1 | 1/2015 | Butterfield et al. |
| 2015/0065988 A1 | 3/2015 | Holderie et al. |
| 2015/0088058 A1* | 3/2015 | Harr ................ A61M 5/14232 604/67 |
| 2015/0093307 A1* | 4/2015 | Gaines ............... F04B 43/1261 422/554 |
| 2016/0015885 A1* | 1/2016 | Pananen ............... G01V 15/00 604/111 |
| 2016/0022545 A1 | 1/2016 | Boulanger et al. |

* cited by examiner ly to a peristaltic pump that delivers fluid in small charges called "aliquots".

CASSETTE FOR A FLOW CONTROL APPARATUS

CROSS-REFERENCE TO RELATED APPLICATION

This application is the nonprovisional application of U.S. Provisional Application Ser. No. 62/771,463 filed Nov. 26, 2018, the entirety of which is incorporated by reference.

FIELD

The present invention generally relates to a flow control system with a flow control apparatus and a feeding set, and more particularly to a cassette for use with the flow control apparatus.

BACKGROUND

Administering medicine or nutrition to a patient who cannot intake the medicine or nutrition orally can be effected by utilizing peristaltic flow control systems. Typically in such systems, fluid is delivered to the patient by a pump set including a flexible elastomeric tubing loaded on a flow control apparatus, such as a peristaltic pump, which delivers fluid to the patient at a controlled rate of delivery. The peristaltic pump usually has a housing that includes a rotor operatively engaged to a motor through a gearbox. The rotor drives fluid through the flexible tubing of the pump set by the peristaltic action effected by reversible compression created by impingement, e.g., pinching, by one or more roller on the rotor. Rotation of the rotor progressively compresses the elastomeric tubing that drives the fluid at a controlled rate. The pump set may have a valve mechanism for permitting or preventing fluid flow communication through the pump set. The flow control system may also have a controller that operatively regulates the one or more motors which effectively controls fluid flow.

Peristaltic pumps operate by delivering fluid in small charges called "aliquots". The rotor engages elastomeric tubing of the pump set, pinching off a portion of the elastomeric tubing and pushing fluid forward of the pinch point, e.g., closer to the patient than to the source of fluid toward the patient. Typically, the volume of fluid to be administered to the patient is controlled in the pump by counting the number of aliquots, each being of substantially the same volume, and stopping when the number reaches an amount corresponding to the total desired volume of fluid to be delivered. Peristaltic pumps are sanitary and generally accurate and therefore very useful in the administration of medication and therapeutic fluids to the patient.

In one aspect, a cassette for use with a pumping apparatus having a pumping system for engaging a pump set generally comprises a cassette body configured for releasable attachment to the pumping apparatus to mount the cassette on the pumping apparatus. A fitting is mounted on the cassette body and includes a mounting structure. At least one identification member is mounted by the mounting structure on the fitting for indicating a functional configuration of the pump set. The mounting structure and identification member are configured to mount the identification member in different orientations on the fitting to indicate different functional configurations of the cassette and pump set.

In another aspect, a fitting assembly for use in a cassette of a pump set generally comprises a body comprising an inlet port and an outlet port. The body is configured for attachment to the cassette. At least one identification member is mounted on the body for indicating a functional configuration of the pump set.

In still another aspect, a cassette for use with a pumping apparatus having a pumping system for engaging a pump set generally comprise a cassette body configured for releasable attachment to the pumping apparatus to mount the cassette on the pumping apparatus. The cassette body has at least one mounting formation. At least one identification member is mounted on the cassette body by the mounting formation of the cassette body. The identification member and mounting formation are formed to mount the identification member in any one of a plurality of predetermined orientations. Each predetermined orientation indicates a different functional configuration of the pump set.

In yet another aspect, a method of assembling a cassette generally comprises providing a cassette for use with a pumping apparatus having a pumping system for engaging a pump set. Mounting at least one identification member to the cassette for indicating a functional configuration of the pump set.

In still yet another aspect, a flow control system generally comprises a flow control apparatus including a pumping device and a sensor. A pump set includes a cassette and tubing mounted to the cassette. The cassette is configured for releasable attachment to the flow control apparatus to mount the cassette and tubing to the flow control apparatus. The cassette has at least one mounting formation and at least one identification member mounted on the cassette by the mounting formation. The identification member and mounting formation are formed to mount the identification member in any one of a plurality of predetermined orientations. Each predetermined orientation indicates a different functional configuration of the pump set. The sensor is configured to detect the presence and orientation of the at least one identification member for determining the functional configuration of the pump set.

BRIEF DESCRIPTION OF THE DRAWINGS

Corresponding reference characters indicate corresponding parts throughout the drawings.

DETAILED DESCRIPTION

One or more aspects of the present invention pertain to peristaltic pumps such as rotary peristaltic pumps and particularly to rotary peristaltic pumps utilizing a cassette having a valve for selecting between a plurality of fluid flow configurations. The cassette also has a configuration for preventing an outlet tube attached to the cassette from kinking. Any one or more advantageous features or structures that provide or facilitate any one or more of such features may be implemented in a peristaltic pump employed in various commercial and industrial applications. Thus, although the detailed discussion is directed to an enteral feed pump with a cassette, any one or more features of the invention may be embodied or implemented in other peristaltic pumps, with or without a cassette. For example, although the exemplarily discussed pump is a rotary peristaltic enteral feeding pump, the present invention has application to other types of peristaltic pumps (not shown), including medical infusion pumps. The general construction and operation of the enteral feeding pump, except as set forth hereinafter, may be generally the same as disclosed in co-assigned U.S. Pat. No. 7,608,059 issued Oct. 27, 2009, entitled FLOW CONTROL APPARATUS; U.S. Pat. No. 7,092,797 issued Aug. 15, 2006, entitled FLOW MONITORING SYSTEM FOR A FLOW CONTROL APPARATUS; and U.S. Pat. No. 7,534,099 issued May 19, 2009, entitled ALIQUOT CORRECTION FOR FEEDING SET DEGRADATION. One or more of the various features and aspects of the invention may be implemented in peristaltic pumps that use mechanisms other than rollers without departing from the scope of the present invention such as linear peristaltic pumps. Moreover, although an exemplary feeding set 7 is shown, other types of pump sets (not shown) can be used without departing from the scope of the present invention.

Figure 1:
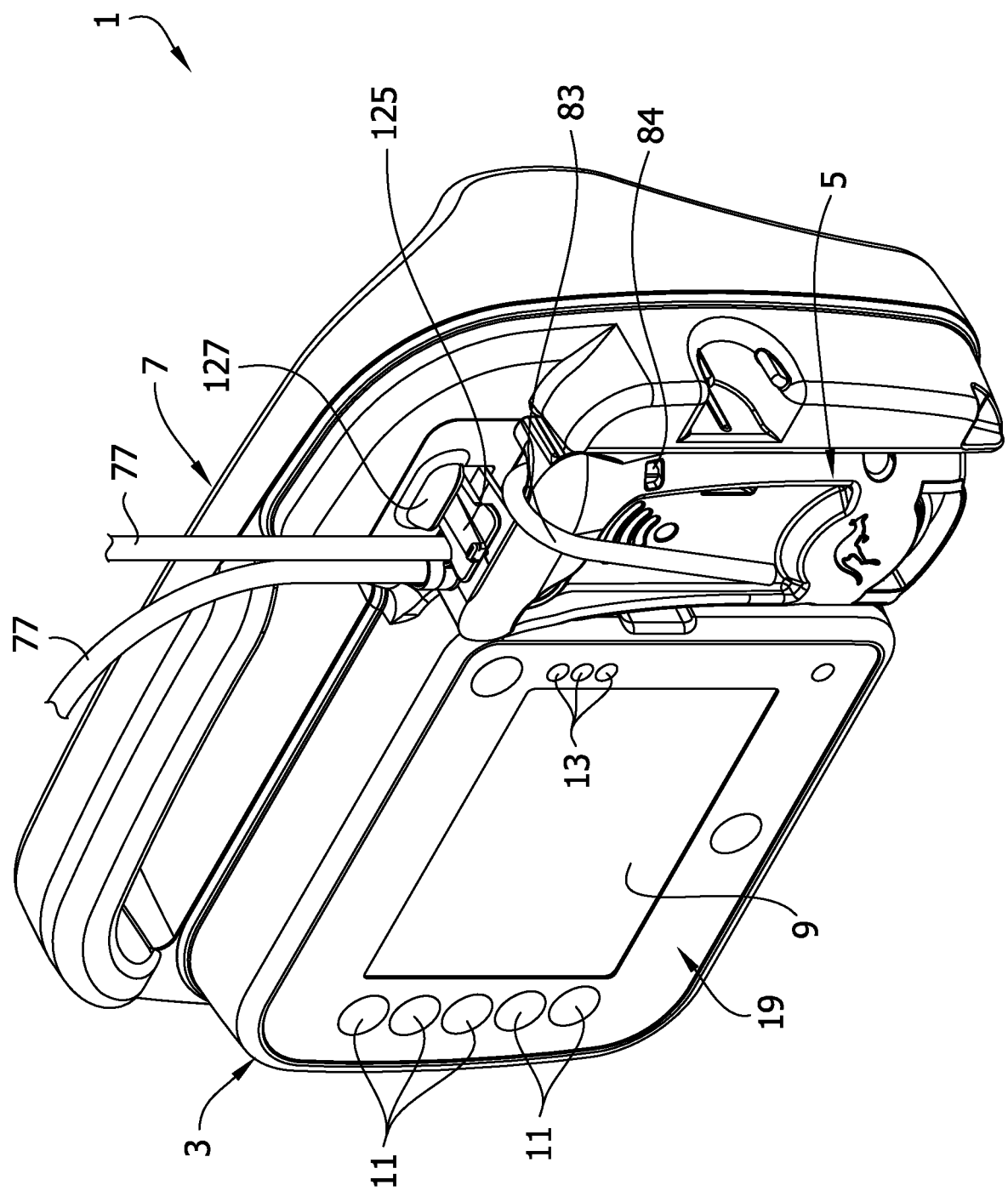
FIG. 1 is a perspective view of a feeding system with a pumping apparatus and a fragmentary portion of a feeding set and a cassette.
Figure 2:
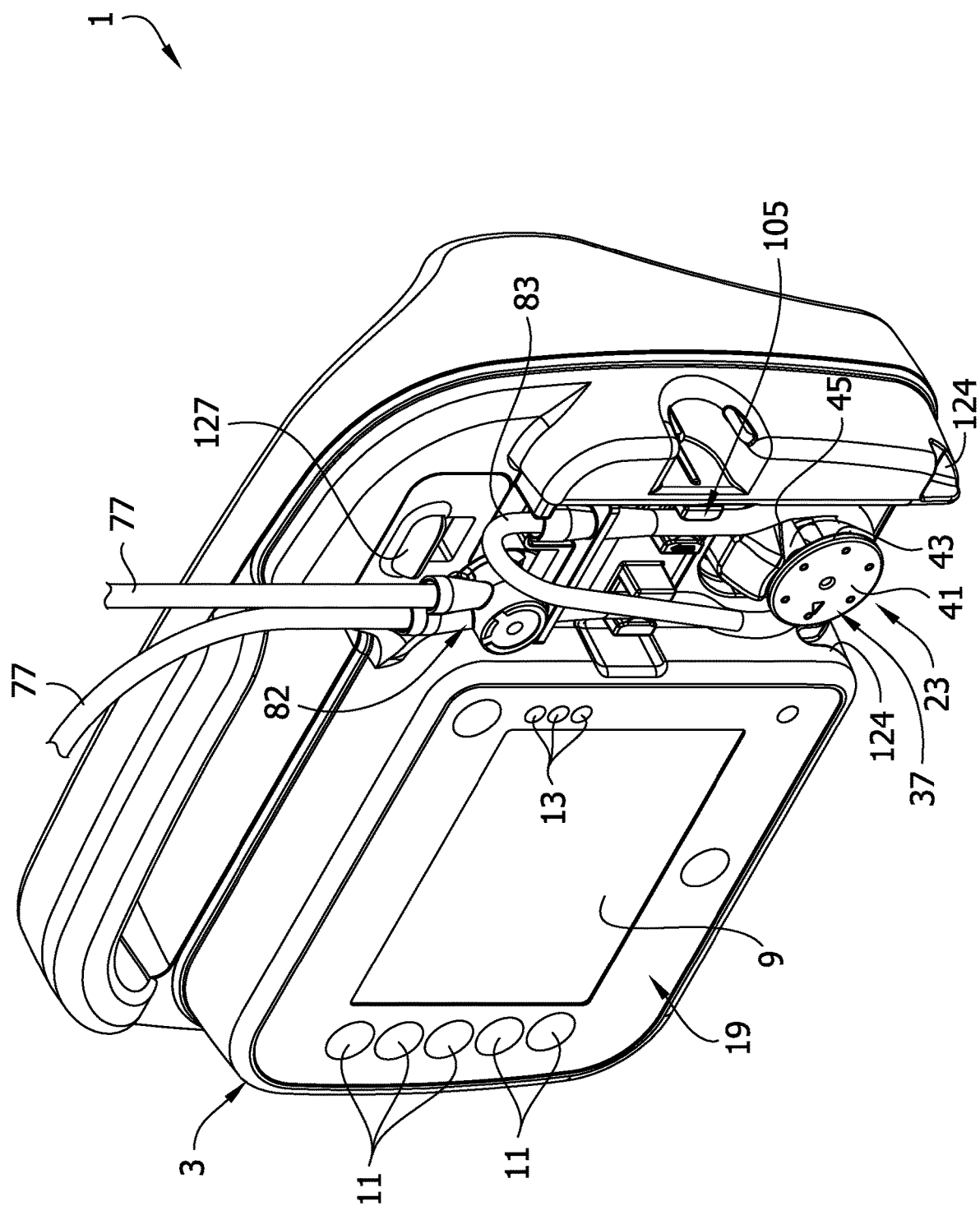
FIG. 2 is a perspective view of the system of FIG. 1, but with portions of the cassette removed.
Figure 3:
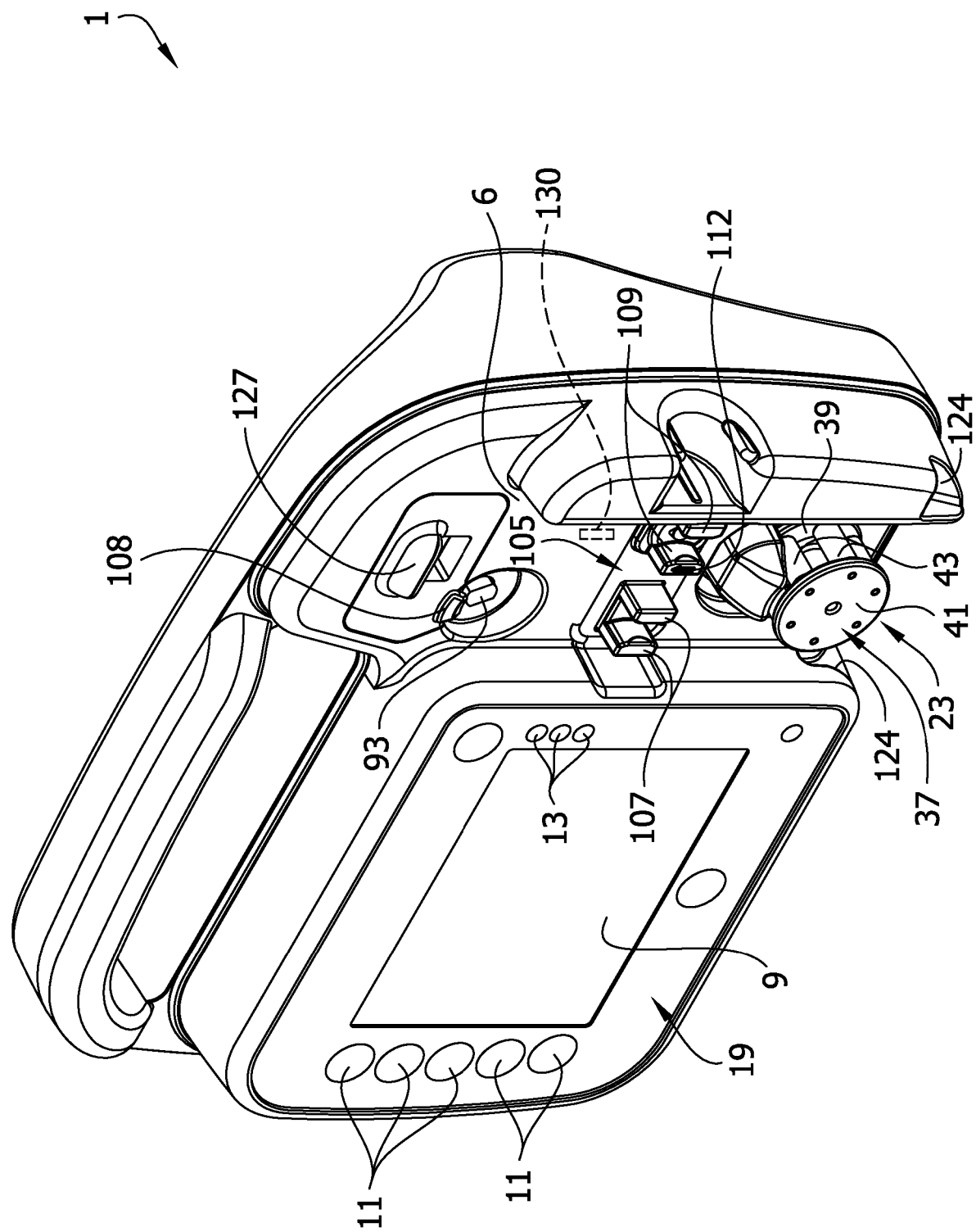
FIG. 3 is the perspective view of FIG. 1 without the feeding set and cassette.

Referring now to the drawings, and in particular FIGS. 1-3, an exemplary enteral feeding pump (broadly, "pumping apparatus") constructed according to the any one or more of the principles of the present invention is generally indicated at 1. The feeding pump may comprise a housing generally indicated at 3 that is constructed so as to mount a cassette, generally indicated at 5, and a feeding set (broadly, a "pump set"), a fragmentary portion generally indicated at 7, removably received in the cassette. The cassette 5 is releaseably attachable to the housing 3. In the illustrated embodiment, the cassette 5 is removably received in a cassette recess 6 in the housing 3 (FIG. 3). It will be appreciated that "housing" as used herein may include many forms of supporting structures (not shown), including without limitation multipart structures and structures that do not enclose or house the working components of the pump 1. Moreover, various aspects and features of the present invention can be implemented without the recess 6. The pump 1 may also have a display screen 9 on the housing 3 that is capable of displaying information about the status and operation of the pump. One or more buttons 11 which can be proximate the display screen 9 can be provided for use in controlling and obtaining information from the pump 1, and one or more light emitting diodes 13 can provide status information for the pump. Legs (not shown) may be disposed at the bottom of the housing 3 to support the housing so that the display screen 9 is angled slightly upward for ease of viewing by a user or operator.

The display screen 9 may be part of a front panel (generally indicated at 19) of the housing 3 and may be removably attached to the housing. The enteral feeding pump may further include a pumping unit indicated generally at 23 comprising a pump motor (not shown) connected to a rotor shaft (not shown). A battery (not shown) may be received in the housing 3 for powering the pump motor. A power source other than or in addition to the battery could be used to energize the pump including one or more prime movers which drive the pumping unit through the rotor shaft.

The pumping unit 23 can have a rotor (generally indicated at 37) which can be coupled to the rotor shaft. The rotor 37 may include an inner disk 39, an outer disk 41, and four rollers 43 (only three of which is shown) mounted between the inner and outer disks for rotation relative to the disks about their longitudinal axes (FIGS. 2 and 3). The rollers 43 engage a tube 45 (FIG. 2) of the feeding set 7 to deliver fluid through the feeding set to a subject when the feeding set is received in the cassette 5 and the cassette is attached to the housing 3. Other numbers of rollers are also envisioned. For example, five or six rollers may also be used without departing from the scope of the disclosure.

Referring to FIGS. 4-7, the cassette 5 may comprise a cassette body 51 having a front 53, a back 55, a top 57, and a bottom 59. Side walls 61 and top wall 63 may extend from the back 55 of the cassette body 51 forming a back cavity configured for receiving a fitting 65. The tube 45 (FIG. 2) may be attached to the fitting 65. The fitting 65 may have tabs 84 that allow the fitting 65 to be secured or snapped into the cassette. In some cases, the fitting can be removably secured to the cassette.

The fitting 65 can comprise a base 67, an inlet port 69, an outlet port 71, and a stem holder 66. The inlet port 69 may include a first attachment portion 73 for insertion into an inlet end of the tube 45, and a pair second attachment portion 75A, 75B for receiving inlet tubing 77 (FIG. 2). The outlet port 71 may include a first attachment portion 79 for engagement or attachment to, such as by insertion into an outlet end of the tube 45, and a second attachment portion 81 for attachment to such as by receiving outlet tubing 83. An opening of the second attachment portion 81 that receives the outlet tubing 83 may funnel or taper down away from the opening to secure the tubing in the opening. The outlet tubing 83 may also be treated with a solvent to soften the tube for insertion into and bonding with the attachment portion 81. Second attachment portion 75A may be placed in fluid communication with a feeding source (e.g., nutrient liquid bag), and second attachment portion 75B may be placed in fluid communication with a flushing source (e.g., flushing fluid bag) via the inlet tubing 77. Alternatively, second attachment portion 75B could be attached to the feeding source and second attachment portion 75A could be attached to the flushing source.

The tube 45, fitting 65, inlet tubing 77, and outlet tubing 83 may comprise the pump set 7. It is also envisioned that the cassette 5 may be considered to be part of the pump set. In a preferred embodiment, the cassette 5 is made from a polymeric material such as polycarbonate.

Figure 13:
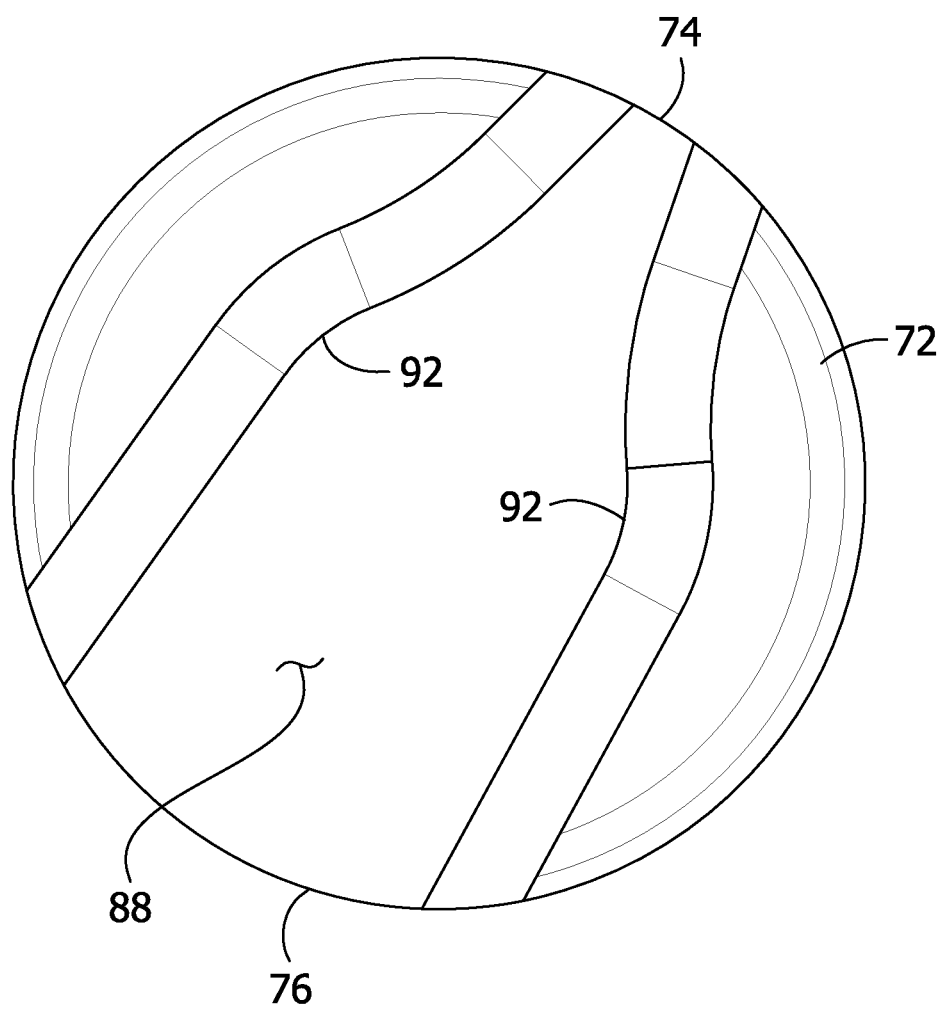
FIG. 13 is a cross section view of the stem.

Referring to FIGS. 8-13, a stopcock including a cylindrical stem 68 is received in a circular opening 70 in the stem holder 66 of the fitting 65. The stem 68 is moveable (i.e. rotatable) in the opening 70 to selectively communicate the second attachment portions 75A, 75B with the first attachment portion 73 for placing the pump set in one of a fluid delivery configuration, a flushing configuration, or a fluid flow blocked configuration. The second attachment portions 75A, 75B each have outlets which communicate with the opening 70 in the fitting 65, and first attachment portion 73 has an inlet that communicates with the opening in the fitting. The stem 68 comprises a cylindrical body 72 having a first opening 74 and a second opening 76 formed in the body. The first and second openings 74, 76 are elongate such that a first dimension of the opening is greater than a second orthogonal dimension. The second opening 76 has a longer slotted dimension than the first opening 74. The first and second openings 74, 76 are located generally on opposite sides of the body 72 and are positioned such that they are in the same plane so that fluid flow through the stem 68 extends downward from the second attachment portions 75A, 75B to the first attachment portion 73 generally within a single plane (FIG. 13). A passage 88 extends within the body 72 of the stem 68 and communicates the first opening 74 with the second opening 76. The passage 88 widens from the first opening 74 to the second opening 76. The passage 88 has curved inner walls 92 giving the passage roughly an inverted V-shaped configuration.

A flange 78 extends radially from the body 72 of the stem 68 and extends partially around a circumference of the body. A cavity 80 is formed in the body 72 which allows a shaft 93 of the pump 1 to engage the body of the stem 68 for rotating the body in the opening 70. The flange 78 is configured to engage a hook 108 in the recess 6 of the pump 1. The engagement between the flange 78 and the hook 108 prevents removal of the feeding set 7 during operation of the pump 1. This safety feature prevents a free flow condition in the feeding set 7 where an uncontrolled amount of fluid is delivered to the patient which can be potentially harmful to the patient. Additionally, the flange 78 functions as a stop engagement feature for limiting rotation of the stem 68 as explained below. The fitting 65 and stem 68 together may be considered a fitting assembly 82. The configuration of the fitting assembly 82 removes the fluid flow selection valve from the inlet tubing 77 and places it within the body of the cassette 5.

Figure 8:
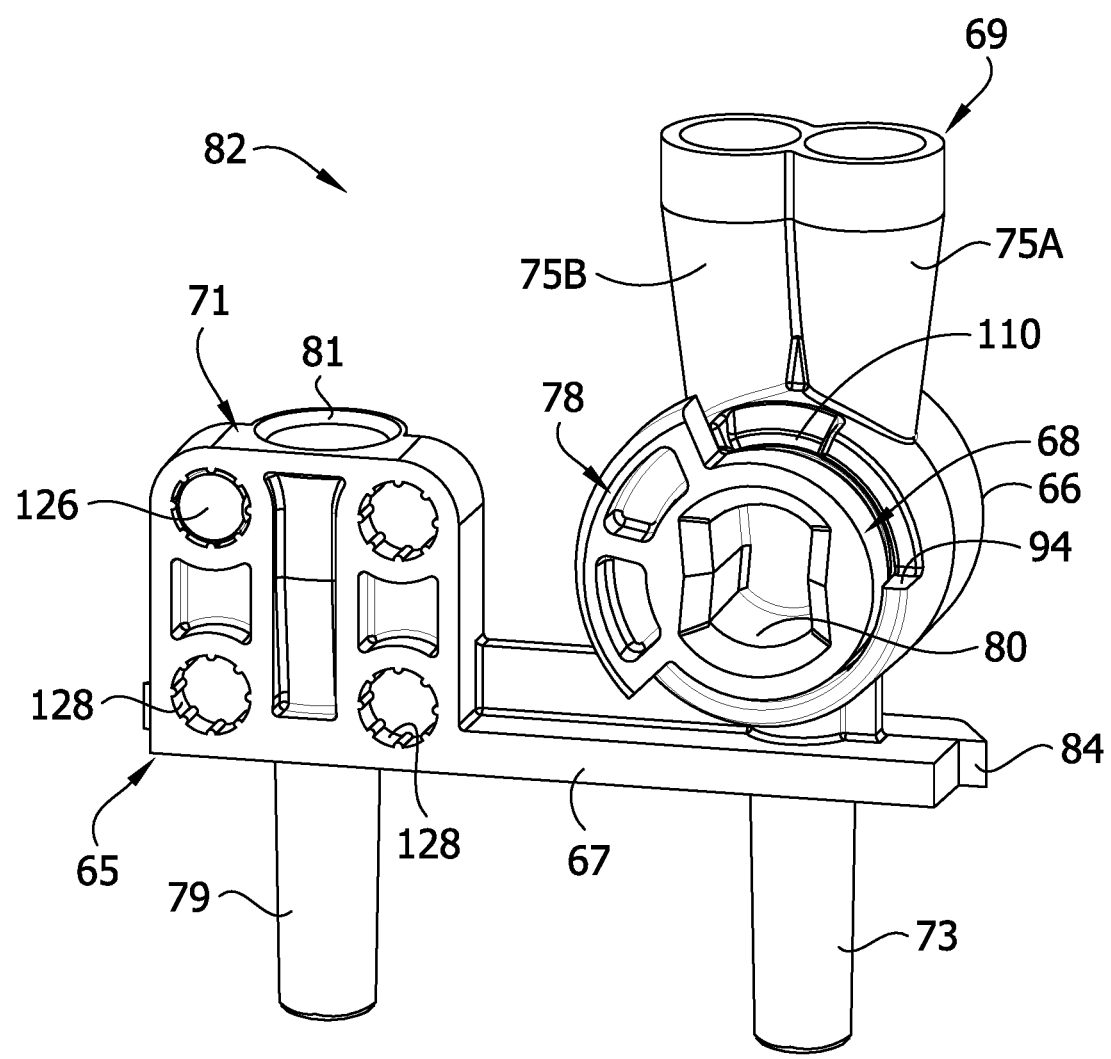
FIG. 8 is a front perspective view of the fitting assembly.
Figure 9:
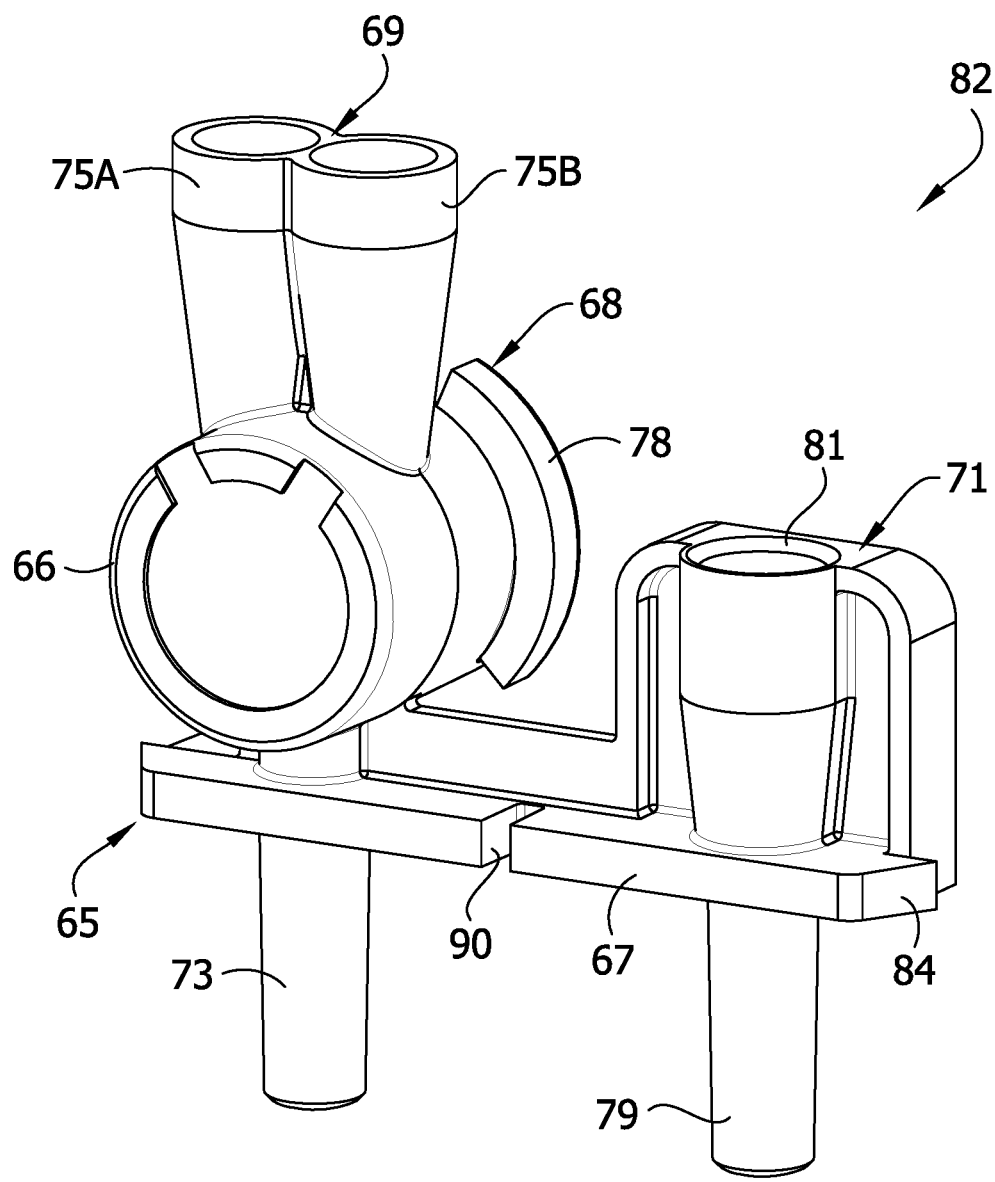
FIG. 9 is a rear perspective view of the fitting assembly.
Figure 10:
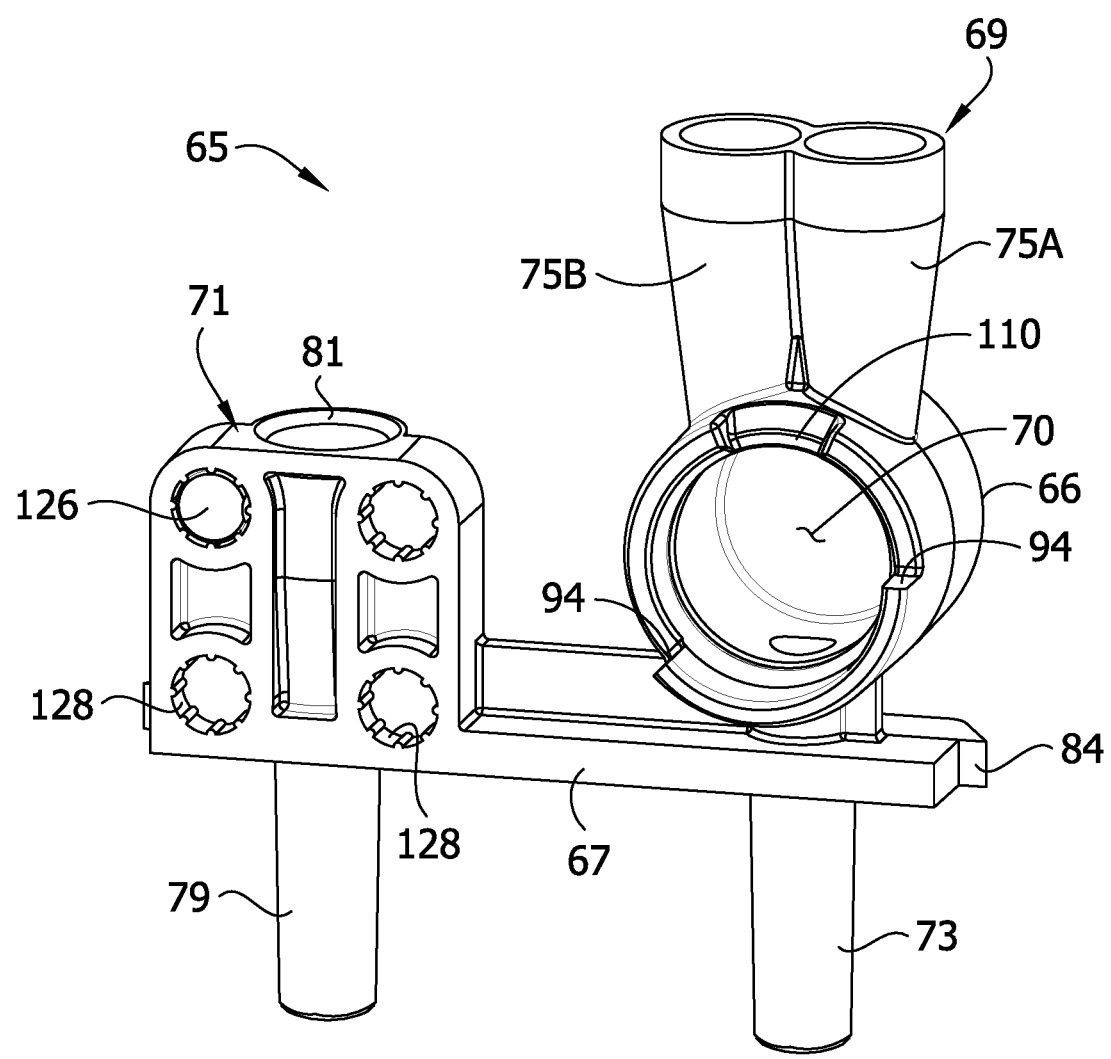
FIG. 10 is a front perspective view of the fitting assembly with a stem of a stopcock removed.
Figure 11:
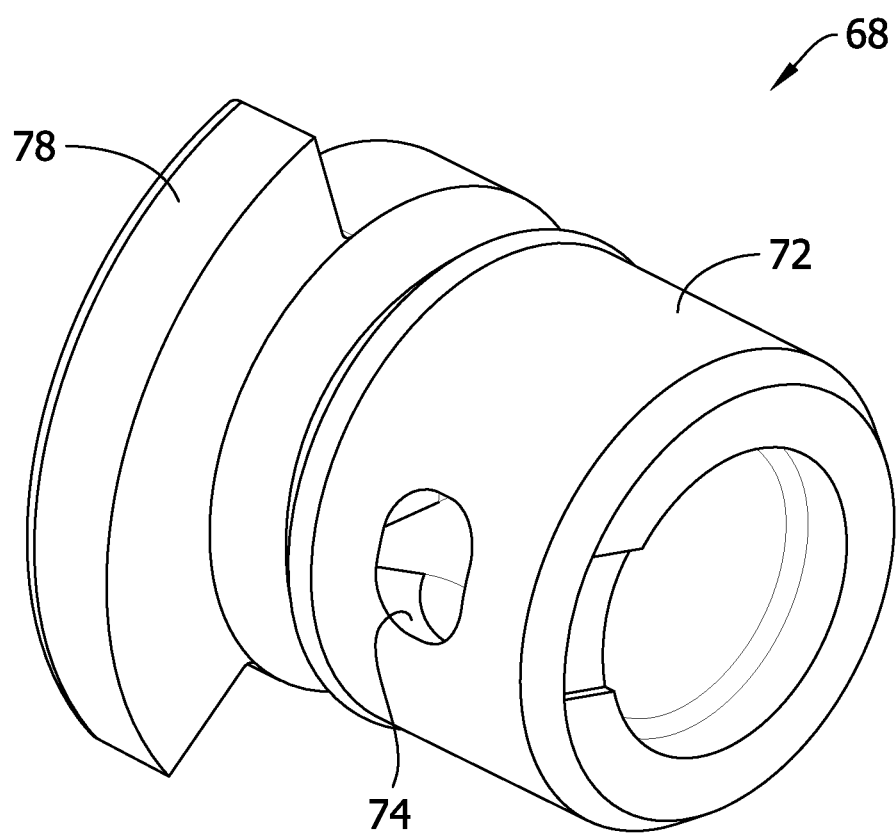
FIG. 11 is a rear perspective view of the stem.
Figure 12:
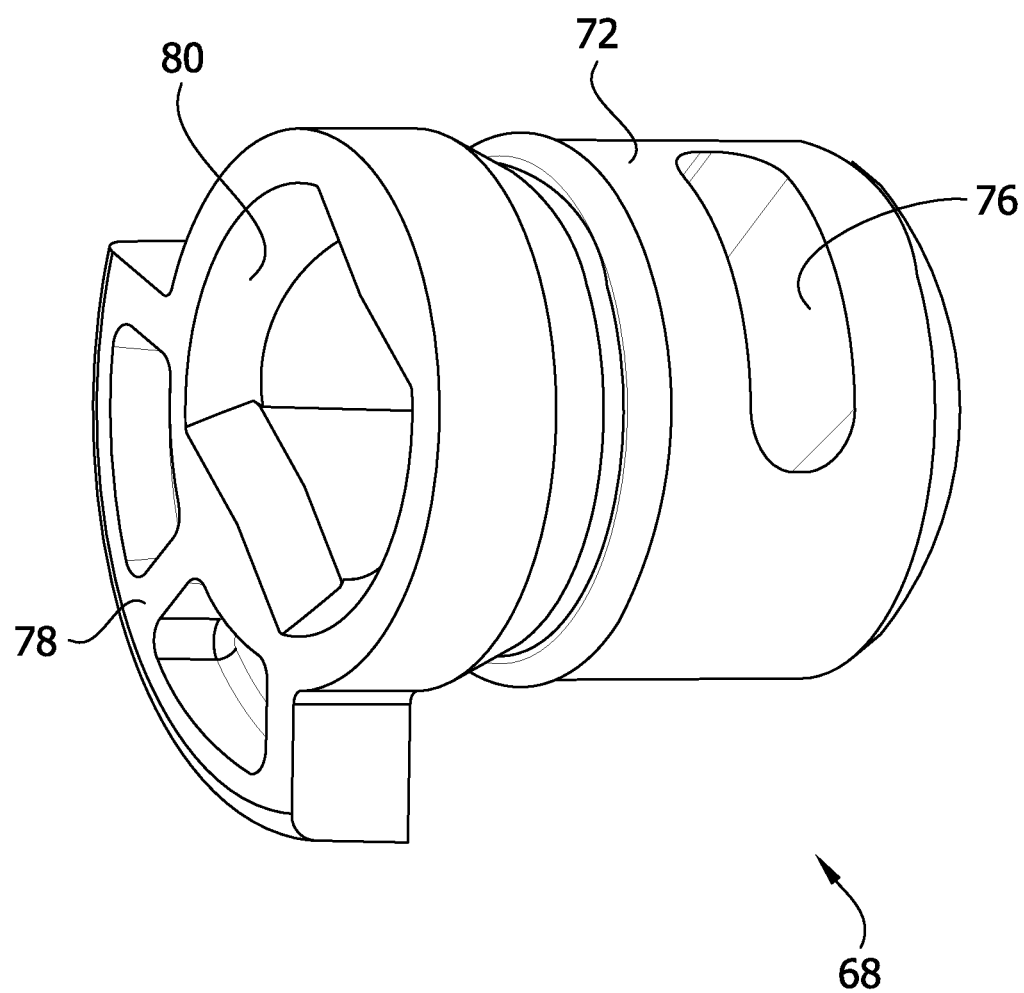
FIG. 12 is a side perspective view of the stem.

In the configuration shown in FIG. 8, the fitting assembly 82 is in the fluid flow blocked configuration where the body 72 blocks the outlets of the second attachment portions 75A, 75B from communicating with the opening 70 and the inlet of the first attachment portion 73. Rotation of the stem 68, such as by the shaft 93 of the pump 1 engaging the cavity 80 and rotating the body 72 clockwise in the opening 70, will place the first opening 74 in communication with the outlet of second attachment portion 75B and the second opening 76 in communication with the inlet of first attachment portion 73 thereby placing the fluid source connected to second attachment portion 75B in fluid communication with the outlet 71 and outlet tubing 83 via tube 45. The second attachment portion 75A remains blocked from communication with the first attachment portion 73. Further rotation of the stem 68 will place the first opening 74 in communication with the outlet of second attachment portion 75A and the second opening 76 will remain in communication with the inlet of the first attachment portion 73 thereby placing the fluid source connected to second attachment portion 75A in communication with the outlet 71 and outlet tubing 83 via tube 45. This is accomplished because the position and length of the second opening 76 are such that at least some portion of the second opening will be in communication with the inlet of the first attachment portion 73 throughout the movement of the stem 68 to communicate the first opening 74 with the outlets of the second attachment portions 75A, 75B. The second attachment portion 75B is now blocked from communication with the first attachment portion 73. Stops 94 on the stem holder 66 engage the flange 78 to limit rotation of the body in the opening 70.

Magnets 126 (broadly, identification members) may be selectively disposed in pockets 128 formed in the outlet port 71 of the fitting. In the illustrated embodiment, only a single magnet 126 is shown. However, up to four (4) magnets 126 can be included where each magnet is received in a respective one of the pockets 128 in the fitting 65. One or more sensors 130 in the pump 1 are positioned near the pockets 128 when the cassette 5 is attached to the pump to detect the presence of the magnets 126 in the pockets 128. In one embodiment, four (4) sensors 130 (only one is illustrated in the drawings) are disposed in the pump opposite the four (4) pockets 128 in the cassette 5 such that a sensor is dedicated to and generally centered on each pocket when the cassette is attached to the pump 1. The number and arrangement of the magnets 126 may be predetermined to indicate a functional configuration of the feeding set 7. For example, the number and arrangement of the magnets 126 may indicate the functional configuration of the feeding set 7 as one of feed, feed/flush, feed wifi, feed/flush wifi, neonatal feed, neonatal feed/flush, neonatal feed wifi, neonatal feed/flush wifi, etc. The sensor 130 along with a processor (not shown) in communication with the sensor is programmed to identify the magnet arrangement as corresponding to a particular functional configuration of the feeding set 7. In one embodiment, the sensor 130 is a Hall-effect sensor. In the illustrated embodiment, the magnets 126 and pockets 128 are disc shaped. However, the magnets 126 and pockets 128 could have other shapes without departing from the scope of the disclosure. Additionally, the magnets 126 can be mounted to the cassette 5 at other locations and by other means without departing from the scope of the disclosure.

Figure 14A:
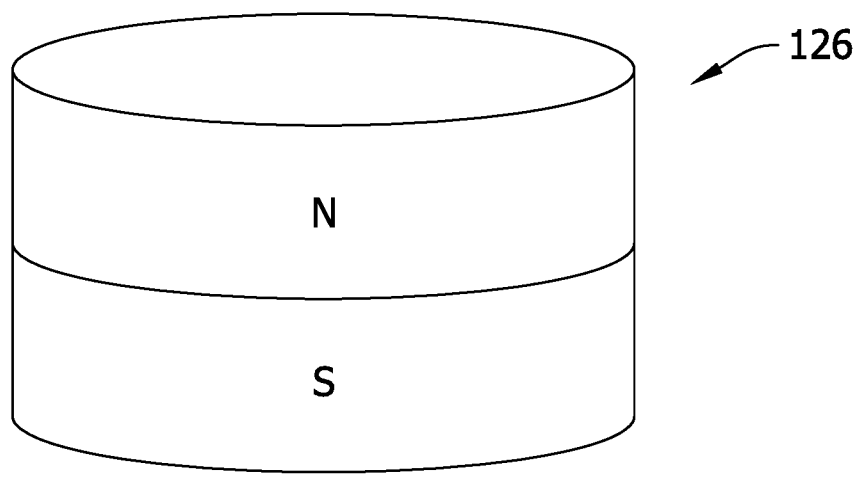
FIG. 14A is a perspective of an axially magnetized magnet.

In one embodiment, the magnets 126 are axially magnetized magnets (FIG. 14A). Thus, for a disc shaped magnet, the north and south poles are formed on opposite circular faces of the disc so that the magnetization direction is along the axis of rotation of the disc. In this embodiment, the magnets 126 can be placed in the pockets 128 with either the north or the south pole facing away from the pocket. In addition to just the presence of a magnet 126 in a pocket 128, the orientation (e.g., facing directions of the north and south poles) of the magnet in the pocket can provide a distinct indication of a particular functional configuration of the feeding set 7. Thus, a magnet 126 at the same location (e.g., within the same pocket 128) on the cassette 5 can provide two, distinct indications to a sensor, depending upon the orientation of the magnet at the location. Therefore, a system that uses one (1) magnet 126, altering which pocket 128 the magnet is received in and the orientation in which the magnet is received in the pocket allows the system to indicate up to eight (8) different magnet position configurations. In a system that uses two (2) magnets 126, altering which pocket 128 each magnet is received in and the orientation in which the magnet is received in the pocket allows the system to indicated up to thirty-two (32) different magnet position configurations. As such, with only two magnets 126, thirty-two (32) feeding set functional configurations can be indicated and identified. A system that uses three (3) magnets 126 can indicate up to sixty-four (64) different magnet position configurations. This provides for the identification of a greater number of functional configurations over a system that only detects magnets as either present or not present.

Figure 14B:
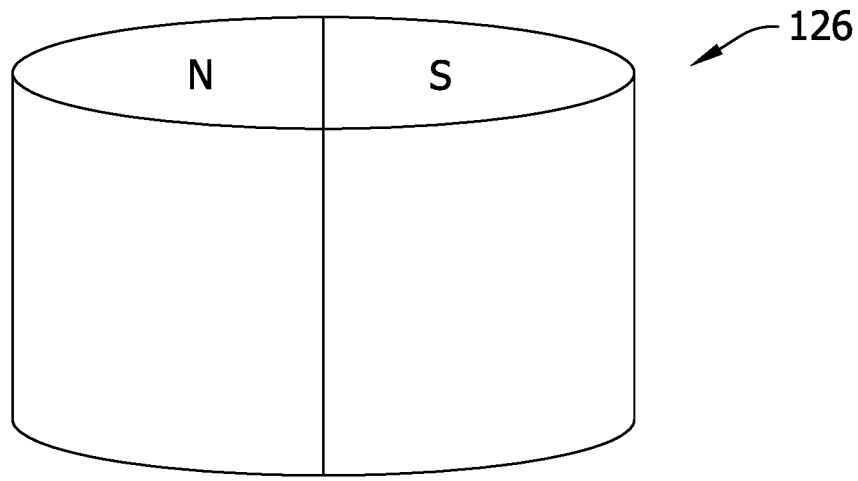
FIG. 14B is a perspective of a diametrically magnetized magnet.

Additionally or alternatively, one or more of the magnets 126 may be diametrically magnetized (FIG. 14B). In the embodiment where the diametrically magnetized magnet is cylindrical or disc shaped, the magnet is magnetized across its diameter so that the magnetization direction is along the diameter of the disc/cylinder. Thus, the north and south poles of the magnet are formed on opposite sides of the magnet. This is in contrast to axially magnetized magnets where, for a disc shaped magnet, the north and south poles are formed on opposite circular faces of the disc so that the magnetization direction is along the axis of the disc. When a diametrically magnetized magnet is used, the sensor 130 in the pump 1 may be an angularity magnet sensor to detect the orientation (i.e., angular position) of the magnet 126 in the pocket 128. The angularity sensor is configured to detect the magnetic field of the magnet and determine the position of the magnet based on the detected magnetic field. For example, the sensor measures the XY coordinates of the magnetic field and determines the magnet's angular position based on the measured coordinates. The magnet 126 can be oriented in different angular positions in a pocket 128 at the same location on the cassette 5 to indicate more than two distinct functional configurations of the feeding set. For example, a particular degree or range of degrees of angular rotation of the magnet 126 may correspond to a particular functional configuration of the feeding set 7. In one embodiment, every 10 degrees of rotation may correspond to a different functional configuration allowing for the identification of thirty-six (36) different functional configurations of the feeding set 7. Other increments of angular rotation are also envisioned for providing a different number of functional configuration identifications. Therefore, only a single magnet may be needed to provide a sufficient number of position variations to indicate the different functional configurations of the feeding set 7. In this embodiment, the four pockets 128 shown in the illustrated embodiment can be replaced with a single pocket to house the single diametrically magnetized magnet. A suitable sensor assembly is the Triaxis® Position Sensor Assembly produced by Melexis, based in Ypres, Belgium.

In one embodiment, the diametrically magnetized magnet 126 is keyed to identify the orientation of the magnet's magnetic field. This allows the system to index which angular positions/magnetic fields correspond to which functional configuration of the feeding set 7.

In one embodiment, the magnets 126 are formed in an unmagnetized condition and then later magnetized. In one embodiment, the magnets 126 are re-magnetized as needed.

Figure 5:
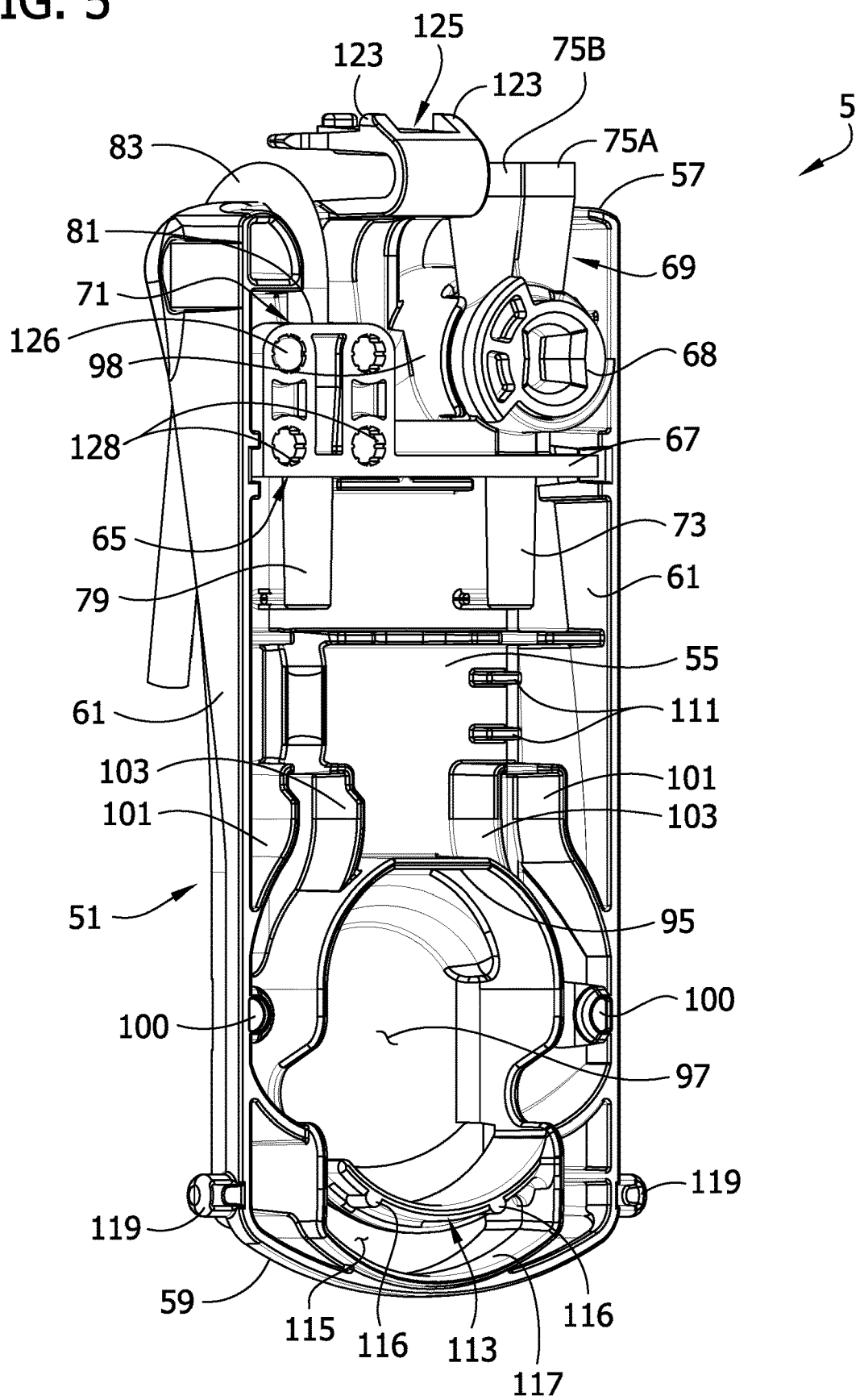
FIG. 5 is a rear perspective view of the cassette.
Figure 6:
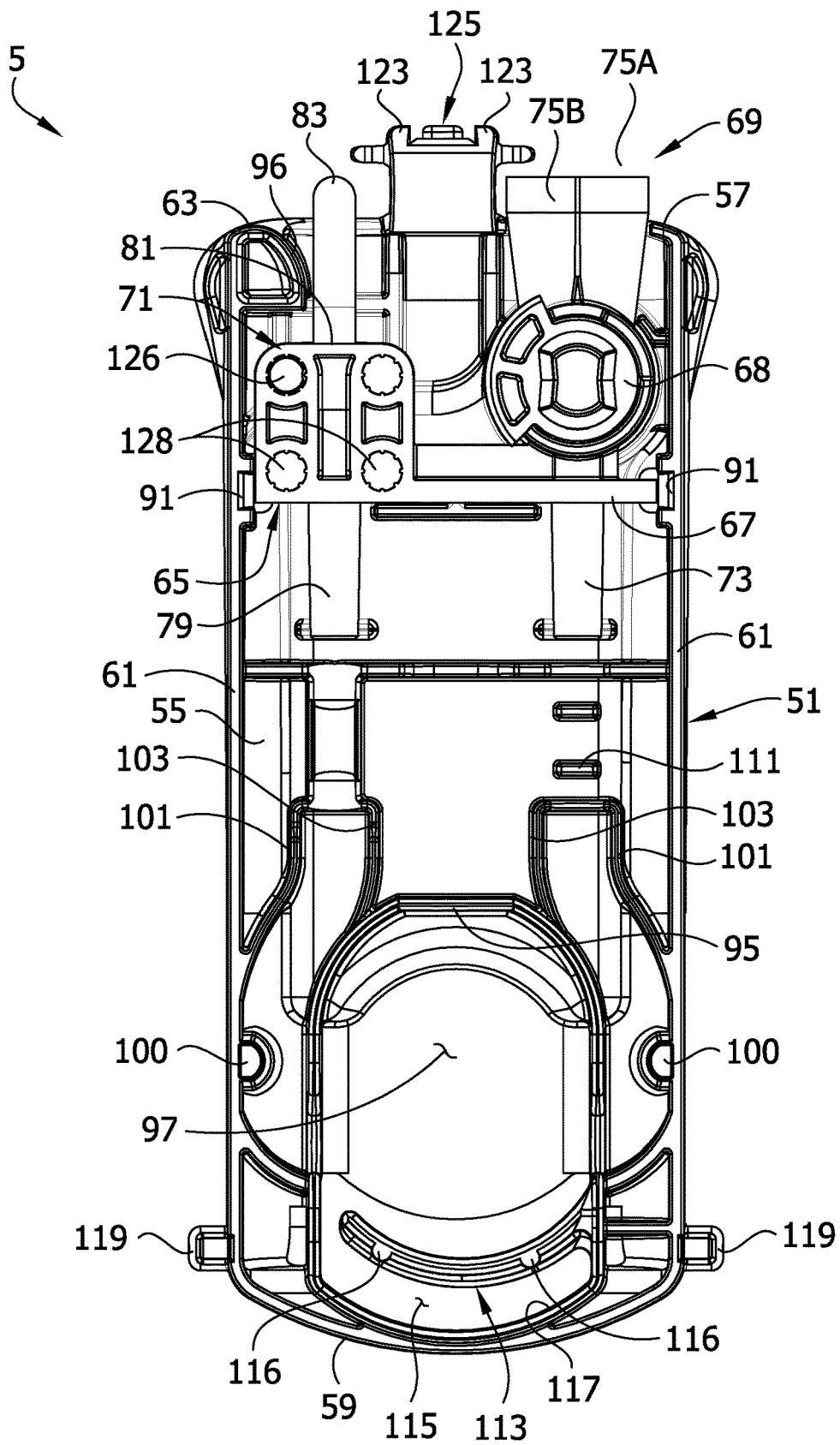
FIG. 6 is a rear elevation view of the cassette.
Figure 7:
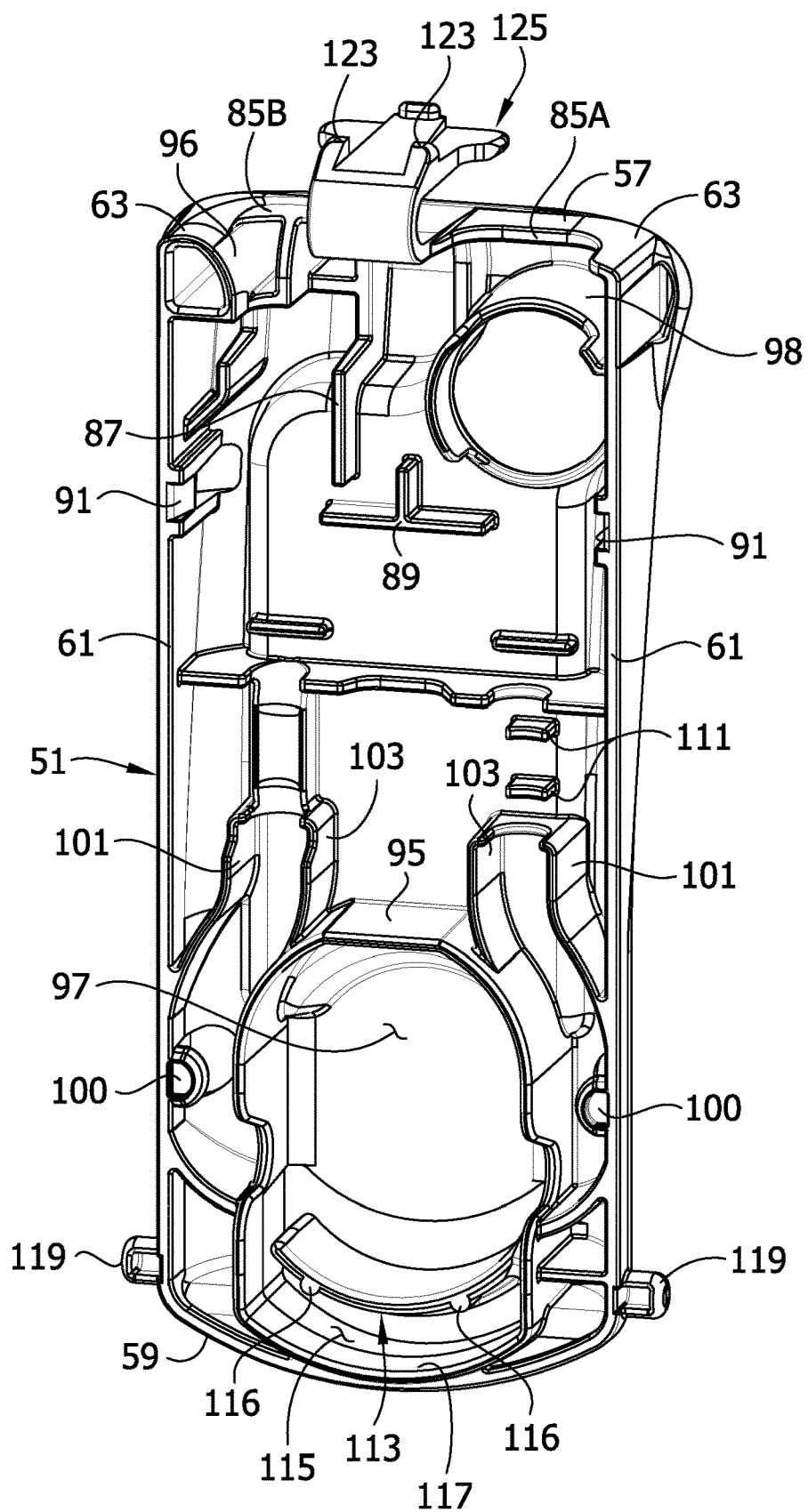
FIG. 7 is the rear perspective view of the cassette with a fitting assembly removed from the cassette.

Referring to FIGS. 5-7, the second attachment portion 81 of the outlet 71 of the fitting 65 is recessed from the top 57 of the cassette 5 so that the outlet tubing 83 extends down into the body 51 of the cassette prior to being inserted into the second attachment portion 81. This provides a section of the outlet tubing 83 that extends adjacent a curved guide wall 96 extending down from the top wall 63. The curved guide wall 96 provides a gradually arced surface for the outlet tubing 83 to rest on preventing the tubing from bending sharply on a transverse edge of the cassette 5. As a result, the outlet tubing 83 is prevented from kinking which can inhibit fluid flow through the tubing. Additionally, because a section of the outlet tubing 83 extends between the top 57 of the cassette 5 and the attachment of the tubing to the fitting 65, the section of the tubing inserted into the second attachment portion 81 which may have been softened by the treatment of the solvent is not located where the tubing is subject to a bending force. Rather, this section is spaced away from the top 57 of the cassette 5 and is held generally straight by the curved guide wall 96. This further reduces the chances of any kinking or pinching off in the outlet tubing 83.

As exemplarily illustrated, tabs 84 (FIGS. 8 and 9) can extend from lateral sides of the base 67 and can be configured to be received in respective openings 86 (e.g., FIGS. 1 and 4) in the front 53 of the cassette 5 to releasably attach the fitting 65 to the cassette. A pair of guide ramps 91 (FIGS. 6 and 7) in the side walls 61 may funnel toward the openings 86. The tabs 84 on the fitting 65 can ride along the ramps 91 and be received in the openings 86 to retain the fitting to the cassette body 51. The stem holder 66 of the fitting 65 is received in a valve holder 98 (FIG. 7) formed in the body 51 of the cassette 5. Alternatively, the fitting 65 may be formed integrally with the cassette body 51, or omitted.

Referring to FIGS. 5 and 7, cutouts 85A, 85B may be formed in the top wall 63 of the cassette body 51 for receiving the second attachment portions 75A, 75B of the inlet port 69 of the fitting 65, and the outlet tubing 83, respectively. A locator wall 87 may extend vertically near the top of the cassette body 51. A T-shaped wall 89 may be disposed between the side walls 61 generally at a center of the cassette body 51. The base 67 of the fitting 65 engages the locator wall 87, and a central extension of the T-shaped wall 89 is received in a recess 90 (FIG. 9) in the base 67. The engagement between the central extension and the recess 90 prevents or at least inhibits any lateral movement of the fitting 65 in the cassette 5. The horizontal portion of the T-shaped wall 89 limits movement of the fitting 65 downward in the cassette 5.

Figure 4:
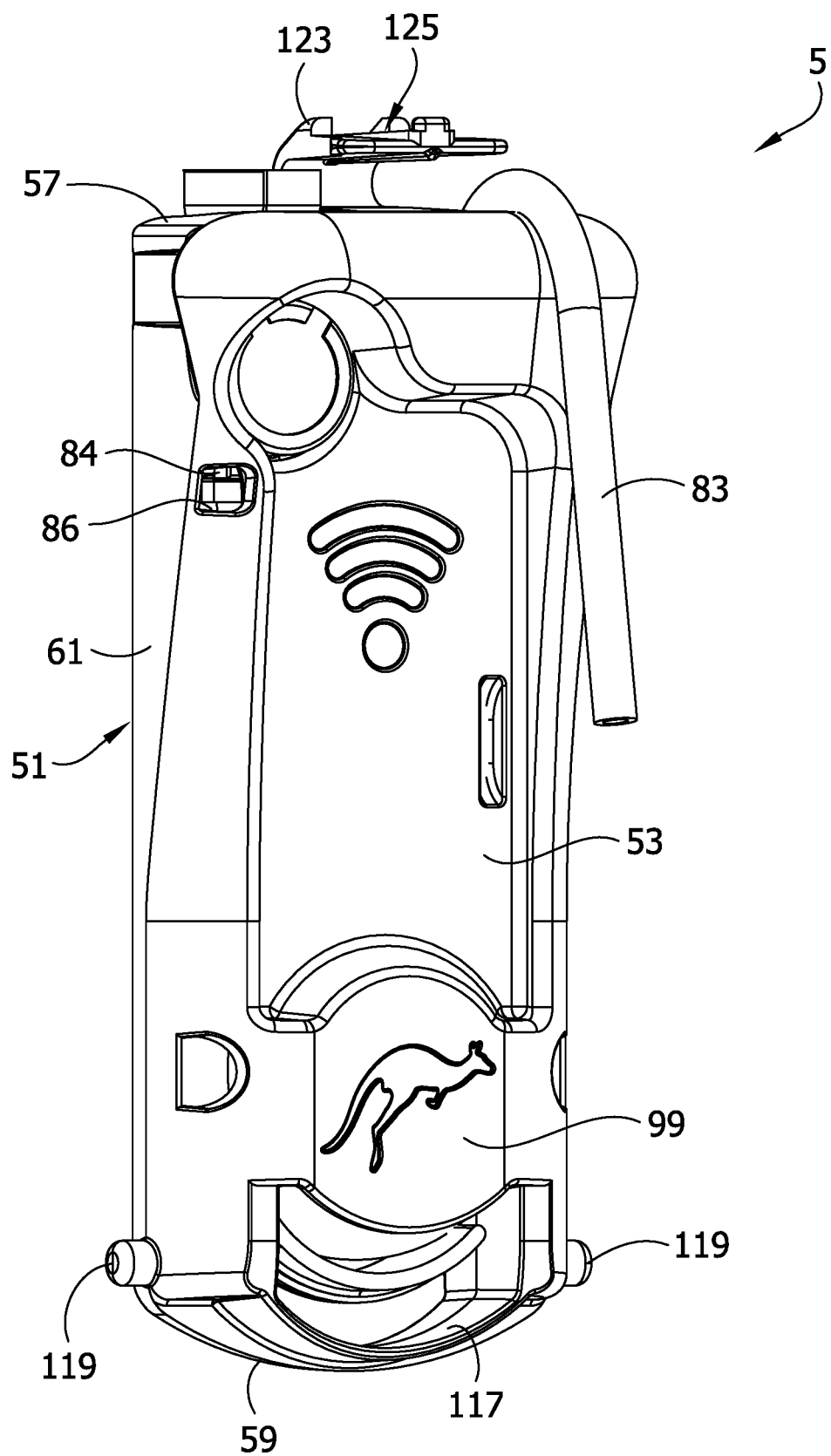
FIG. 4 is front perspective view of the cassette.

An arcuate wall 95 may be disposed generally at a middle of the cassette body 51 to at least partially define a rotor recess 97 for receiving at least a portion of the rotor 37 of the pump 1 when the cassette 5 is attached to the housing 3. The rotor recess 97 may include a bump-out 99 on the front 53 of the cassette body 51 (FIG. 4). Inlet and outlet outer curved guide walls 101 may extend generally parallel to opposite sides of arcuate wall 95. Inlet and outlet inner curved guide walls 103 may extend upward from the arcuate wall 95 generally parallel to the inlet and outlet outer curved guide walls 101, respectively, forming inlet and outlet openings for receiving and supporting respective inlet and outlet portions of the tube 45. The guide walls 101, 103 and arcuate wall 95 may form a tube channel for receiving a lower portion of the tube 45 in a looped configuration to properly position the tube relative to the rotor 37 when the cassette 5 is attached to the housing 3. The arcuate wall 95 and curved guide walls 101, 103 may receive the tube in close fitting relation around the sides of the rotor recess 97. Tabs 100 may extend over the tube channel to hold the tube 45 in the tube channel and to retain the tube 45 in the cassette, constraining the tube according to a third axis. The outer curved guide walls 101 may terminate generally at a bottom side of the rotor recess 97 so that the tube 45 is not directly opposed by the guide walls 101, 103 or the arcuate wall 95 at the bottom of the rotor recess 97.

An insert 105 may be received in the cassette recess 6 in the housing 3 to aid in securing the cassette 5 and tube 45 in the cassette recess 6 (FIG. 3). The insert 105 may be positioned in the recess 6 such that the insert 105 is received in the back cavity of the cassette 5 above the curved guide walls 101, 103 when the cassette 5 is attached to the housing 3. The insert 105 may comprise a pair of opposing first projections 107 disposed at an inlet side of the insert for receiving the inlet portion of the tube 45, and a pair of opposing second projections 109 disposed at an outlet side of the insert for receiving the outlet portion of the tube. Ribs 111 (FIGS. 6 and 7) on the back 55 of the cassette body 51 may be positioned to engage the outlet portions of the tube 45 between the second projections 109 to aid in inserting the inlet and outlet portions into the projections. Indicia 112 may be disposed on at least one of the second projections 109 indicating the direction of fluid flow in the tube 45. In the illustrated embodiment, the indicia 112 is in the form of an arrow.

Referring to FIGS. 5-7, a stator member 113 may be disposed a bottom portion of the cassette body 51 in a cavity such as stator opening 115 generally at or proximate the bottom of the rotor recess 97. Thus, when the cassette 5 is attached to the housing 3, the stator member 113 is typically positioned generally opposite a bottom of the rotor 37. In advantageous configurations, the stator member 113 may support the tube 45 of the feeding set 7 when the rollers 43 engage the tube, as explained below. In some cases, the stator member 113 may have an arcuate shape extending along a length of the stator member. As in the exemplarily illustrated embodiments, the stator member 113 may be a cantilevered member anchored only at a first end to the cassette body 51 and at least partially free to float in the stator opening 115 relative to the cassette body 51. As shown, the flexible stator member 113 may pivot about its connection or anchor to the remainder of the cassette 5 and may flatten out. For example, the stator member can have the first end affixed to the cassette body and a second end that is unfixed which can float or be displaced to allow a reaction segment having a surface of the stator member to have a deflection displacement. For example, as the at least one roller traverses along the tube while revolving about the axis of rotation of the rotor, the flexible stator member 113 may be displaced or deflect to a deflection displacement in reaction to the applied force by the one or more rollers 43 during revolution thereof about the axis of rotation.

Transverse ribs 116 on a bottom of the first section can provide structural rigidity to the flexible stator member 113 and can serve as contacting surfaces that facilitate removal, such as by ejection, of the cantilevered member from a mold cavity. In the illustrated embodiment, the flexible stator member 113 may be integrally formed as one piece with the cassette body 51. However, the flexible stator member 113 could be formed separately from the cassette body 51 and attached to the cassette body by a suitable means. For example, a flexible stator (not shown) can have an elongate extension portion that is engaged in an engagement cavity in the cassette body wherein the engagement cavity is correspondingly sized and shaped to receive the extension portion. In this manner, a stator member can be selected from a plurality of candidates of differing mechanical characteristics, such as modulus and radius of curvature, to tailor the cassette operating parameters, with or without consideration for any of the tube characteristics, and provide specific flow performance attributes during pumping operation.

A stop 117 may be disposed at a bottom of the stator opening 115 to limit the floating movement of the flexible stator member 113 to a maximum displacement. The stop 117 may be spaced relative to the underside of the flexible stator member 113 to prevent flexing of the stator member that would result in plastic deformation of the stator member. For example, the stop member may be positioned to limit the magnitude of the deflection displacement distance of the unfixed end to the maximum displacement. In the illustrated embodiment, the stop 117 is formed as part of the cassette body 51. However, the stop 117 could be formed separately from the cassette body 51 and attached to the cassette body in a suitable fashion. In other cases, stop 117 may be formed on the housing 3 and configured to limit the displacement of the flexible stator member 113 to the maximum displacement. The stop 117 may have a width that is greater than the width of the flexible stator member 113 so that the stop provides an adequate surface area to limit movement of the stator member. The stop 117 can serve to shield the flexible stator member 113 and is typically sized to prevent or reduce the likelihood of snagging or catching the member 113.

Prior to attaching the cassette 5 to the pump housing 3, the inlet and outlet tubing 77, 83 may be attached to the inlet and outlet ports 69, 71, respectively, of the cassette. To attach the cassette 5 to the pump housing 3, one or more pins or raised projections 119 at the bottom 59 of the cassette body 51 may be inserted in slots 124 at the bottom of the recess 6 in the housing 3. The engagement between the raised projections 119 and slots 124 generally locates the cassette 5 on the housing 3. The cassette body 51 can then be rotated up until ledges 123 on a tab 125 at the top 57 of the cassette body are captured by a catch 127 at the top of the recess 6. In the illustrated embodiment, the raised projections 119 and ledges 123 are formed integrally with the cassette body 51. However, the raised projections 119 and ledges 123 can be formed separately from the cassette body 51 and attached to the cassette body in a suitable fashion. After attachment of the cassette 5 to the pump housing 3 the pockets 128 in the fitting 65 will be generally disposed opposite the one or more sensors 130 in the pump 1. In this position, the one or more sensors 130 can detect any magnets 126 received in the pockets 128, and the orientation of the magnets in the pockets, to determine the functional configuration of the feeding set 7. Knowing the functional configuration of the feeding set 7 instructs the pump 1 on what pumping routines to execute. To detach the cassette 5 from the pump housing 3, the tab 125 can be depressed to disengage the ledges 123 from the catch 127.

Once the cassette 5 is attached to the pump housing 3, the tube 45 of the feeding set 7 is positioned for engagement by the rollers 43 of the pump 1. The rollers 43 engage the tube 45 at portions of the tube supported by the flexible stator member 113. Engagement of the tube 45 by a roller 43 causes the flexible stator member 113 to flex or move away from the roller. In particular, the movement allows the tube 45 to at least partially straighten out into a more linear configuration permitting the rollers 43 to occlude the tube in a semi-linear fashion. Therefore, instead of pulling and stretching the tube 45 as can be the case with rollers in conventional pumps, the rollers 43 slide along the tube and occlude the tube in a reduced tension state. As a result, the rollers 43 produce aliquots consistent with the actual linear dimensions of the tube 45. Accordingly, the calculated aliquot volume of the pump 1 more closely matches the actual aliquot volume produced by the pump resulting in more accurate feeding.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions without departing from the scope of the invention, it is intended that all matter contained in the above description and shown in the accompanying drawings shall be interpreted as illustrative and not in a limiting sense.

What is claimed:

1. A cassette for use with a pumping apparatus having a pumping system for engaging a pump set, the cassette comprising:
    a cassette body configured for releasable attachment to the pumping apparatus to mount the cassette on the pumping apparatus, the pumping apparatus having at least one sensor configured to detect presence and orientation of at least one identification member when the cassette is engaged with the pumping apparatus;

a fitting assembly mounted on the cassette body, the fitting assembly comprising at least one mounting formation, an inlet port, an outlet port and tubing connecting the inlet port to the outlet port, with the inlet port being configured to receive at least one of an external feeding source or an external flushing source;

the at least one mounting formation comprising a plurality of pockets with each pocket configured to receive one identification member of the at least one identification member in any one of a plurality of predetermined orientations, each predetermined orientation indicating a different functional configuration of the pump set based on the presence and orientation of the at least one identification member when the cassette is engaged with the pumping apparatus and the cassette body aligning the fitting assembly with the pumping apparatus such that the at least one sensor detects the at least one identification member; and the cassette further comprising the at least one identification member positioned in at least one pocket of the plurality of pockets.

2. The cassette of claim 1, wherein each sensor is a Hall-effect sensor.

3. The cassette of claim 1, wherein each pocket of the plurality pockets is positioned to be centered on a corresponding sensor of the pumping apparatus when the cassette is engaged with the pumping apparatus.

4. The cassette of claim 1, wherein the pumping apparatus further comprises a processor in communication with the at least one sensor, the processor configured to identify the functional configuration of the pump set based on the presence and orientation of the at least one identification member when the cassette is engaged with the pumping apparatus and the at least one identification member is detected by the at least one sensor.

5. The cassette of claim 4, wherein the functional configuration of the pump set is one of feed, feed/flush, feed wifi, feed/flush wifi, neonatal feed, neonatal feed/flush, neonatal feed wifi, and neonatal feed/flush wifi.

6. The cassette of claim 1, wherein the fitting assembly further comprises a stem holder.

7. The cassette of claim 1, wherein the fitting assembly comprises two tabs configured to secure or snap the fitting assembly to the cassette body.

8. The cassette of claim 1, wherein the plurality of pockets comprises four pockets with each pocket configured to receive one identification member of the at least one identification member.

9. The cassette of claim 8, wherein the at least one sensor comprises four sensors.

10. The cassette of claim 1, wherein the at least one identification member comprises a single identification member, the single identification member and the at least one mounting formation being configured to indicate one functional configuration of eight different functional configurations.

11. The cassette of claim 10, wherein the functional configuration of the pump set is one of feed, feed/flush, feed wifi, feed/flush wifi, neonatal feed, neonatal feed/flush, neonatal feed wifi, and neonatal feed/flush wifi.

12. The cassette of claim 1, wherein the at least one identification member is a single magnet and resides in one pocket of the plurality of pockets.

13. The cassette of claim 12, wherein the single magnet and each pocket of the plurality of pockets being disc shaped.

14. The cassette of claim 1, wherein the at least one identification member is one of an axially magnetized magnet and a diametrically magnetized magnet.

15. The cassette of claim 1, wherein the at least one identification member is an axially magnetized magnet, and the plurality of predetermined orientations include one of a north and south pole of the magnet facing in a first direction, and said one of the north and south pole of the magnet facing in a second direction, opposite the first direction.

16. The cassette of claim 1, wherein the at least one identification member is a diametrically magnetized magnet, and the plurality of predetermined orientations include multiple angular positions of the magnet.

17. The cassette of claim 16, wherein the at least one sensor is an angularity magnet sensor configured to detect an angular position of the diametrically magnetized magnet.

18. The cassette of claim 1, wherein the at least one identification member comprises a plurality of identification members.

19. The cassette of claim 1, wherein the at least one identification member comprises two identification members, the two identification members and the at least one mounting formation being configured to indicate up to thirty-two different functional configurations.

20. The cassette of claim 1, wherein the cassette body defines a housing having an interior that receives at least a portion of the tubing.

* * * * *